(12) United States Patent
Tokita et al.

(10) Patent No.: US 8,540,637 B2
(45) Date of Patent: Sep. 24, 2013

(54) BIOLOGICAL INFORMATION ACQUISITION APPARATUS AND BIOLOGICAL INFORMATION ACQUISITION METHOD

(75) Inventors: Toshinobu Tokita, Yokohama (JP);
Kazuhiko Fukutani, Yokohama (JP);
Takao Nakajima, Kawasaki (JP);
Katsumi Nakagawa, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 139 days.

(21) Appl. No.: 13/140,816

(22) PCT Filed: Dec. 16, 2009

(86) PCT No.: PCT/JP2009/071369
§ 371 (c)(1),
(2), (4) Date: Jun. 17, 2011

(87) PCT Pub. No.: WO2010/074104
PCT Pub. Date: Jul. 1, 2010

(65) Prior Publication Data
US 2011/0251475 A1  Oct. 13, 2011

(30) Foreign Application Priority Data
Dec. 25, 2008 (JP) ................... 2008-330365
Oct. 16, 2009 (JP) ................... 2009-239400

(51) Int. Cl.
*A61B 8/00* (2006.01)
(52) U.S. Cl.
USPC ........................................ 600/443; 600/437
(58) Field of Classification Search
USPC ................. 600/425, 427, 437, 443, 444, 448; 73/625, 626
See application file for complete search history.

(56) References Cited

U.S. PATENT DOCUMENTS

| 5,027,658 A | 7/1991 | Anderson |
| 6,607,489 B2 | 8/2003 | Hoctor et al. |
| 2002/0099290 A1 | 7/2002 | Haddad |
| 2006/0079777 A1 | 4/2006 | Karasawa |
| 2006/0235302 A1 | 10/2006 | Grossman et al. |
| 2008/0242979 A1 | 10/2008 | Fisher et al. |

FOREIGN PATENT DOCUMENTS

JP  2006-095002 A1  4/2006

OTHER PUBLICATIONS

Manohar et al, "The Twente Photoacoustic Mammoscope: System Overview and Performance", Physics in Medicine and Biology, vol. 50, May 18, 2005, pp. 2543-2557, IOP Publishing Ltd.
Liu et al., "Propagation and Backpropagation for Ultrasonic Wavefront Design" IEEE Transactions on Ultrasonics, Ferroelectrics and Frequency Control, vol. 44, No. 1, Jan. 1, 1997, pp. 1-13.

*Primary Examiner* — Michael Rozanski
(74) *Attorney, Agent, or Firm* — Canon U.S.A., Inc. IP Division

(57) ABSTRACT

When a subject is pressed by a plate and an acoustic wave is received by a probe via the plate, the acoustic wave is refracted because of the difference between a sound velocity in the subject and a sound velocity in the plate. When the refraction is not considered, a reduction in resolution occurs. Weights for signals or virtual wavefronts corresponding to the signals to be added to one another are determined using a thickness of the plate, the sound velocity in the plate, the sound velocity in the subject, positions of image elements (pixels or voxels) for image information, and arrival times of the acoustic wave from an object that is a sound source. The signals or the virtual wavefronts corresponding to the signals are added to one another, thereby acquiring the image information.

12 Claims, 11 Drawing Sheets

BIOLOGICAL INFORMATION ACQUISITION APPARATUS AND BIOLOGICAL INFORMATION ACQUISITION METHOD

CROSS-REFERENCE TO RELATED APPLICATIONS

This application claims the benefit of Japanese Patent Applications No. 2008-330365, filed Dec. 25, 2008, and No. 2009-239400, filed Oct. 16, 2009, which are hereby incorporated by reference herein in their entirety.

TECHNICAL FIELD

The present invention relates to a biological information acquisition apparatus and a biological information acquisition method for performing image reconstruction using an acoustic wave that is emitted from the inside of a subject.

BACKGROUND ART

There is a photoacoustic apparatus that has been developed for breast cancer screening as a biological information acquisition apparatus of the related art that is described in Non Patent Citation. The biological information acquisition apparatus that is described in Non Patent Citation presses a subject (a breast) with a glass plate and an ultrasound probe, and irradiates the subject via the glass plate with illumination light (near-infrared light) that is emitted from a light source which is an Nd:YAG laser. Then, the biological information acquisition apparatus receives, with the probe, a photoacoustic wave that is an acoustic wave generated inside the subject, and generates and displays an image of tissue inside the subject, in particular, an image of breast cancer angiogenesis. An operation for image generation in such a manner is called image reconstruction. Note that a polymer with a thickness of 18.6 mm is provided on the surface of the probe. Because a sound velocity of a sound propagating through the polymer is different from a sound velocity of a sound propagating through the subject, the photoacoustic wave is refracted by the polymer before the photoacoustic wave is received by the probe. When refraction of a photoacoustic wave is not considered in image reconstruction, a reduction in resolution occurs.

A method for solving the above-mentioned issue is described in Patent Citation. In Patent Citation, a multifunction apparatus in which an X-ray mammography and an ultrasound apparatus are combined together is described. The X-ray mammography presses a subject using a compression plate that is used as a subject holding member, obtains information concerning X-rays by causing the X-rays to pass through the subject, and performs imaging in accordance with the information concerning X-rays. When the ultrasound apparatus is combined with the X-ray mammography, an ultrasound probe transmits/receives an ultrasound wave via the compression plate. Accordingly, referring to FIG. 11, delay times associated with reception of the ultrasound wave using individual transformation elements (the differences among arrival times at the ultrasound wave arrived at the individual transformation elements) are calculated so that correction is performed for refraction of the ultrasound wave which occurred due to the difference between a sound velocity in the compression plate and a sound velocity in the subject. Electric signals that are obtained by the individual transformation elements are added to one another. In FIG. 11, $c_1$ and $c_2$ are the sound velocity of a sound propagating through the compression plate and the sound velocity of a sound propagating through the subject, respectively. $L_1$, $L_2$, $R_1$, $R_2$, and D denote individual distances. $\beta_1$ and $\beta_2$ are angles.

PATENT CITATION

U.S. Pat. No. 6,607,489

NON PATENT CITATION

Srirang Manohar, et al., The Twente photoacoustic mammoscope: system overview and performance, Physics in Medicine and Biology 50 (2005) 2543-2557

DISCLOSURE OF INVENTION

Correction for refraction in image reconstruction is not described in Non Patent Citation. The photoacoustic wave that is emitted from the subject is refracted by the polymer, and this leads to a reduction in resolution. Patent Citation aims to solve the above-mentioned issue. However, in the multifunction apparatus described in the Patent Citation, refraction is not considered in an apodization technique (weighting) for electric signals to be subjected to processing using a delay-and-sum. Thus, this leads to a reduction in resolution.

The present invention aims to solve the above-mentioned issues of the background art. The present invention provides a biological information acquisition apparatus and a biological information acquisition method in which a reduction in resolution associated with refraction of an acoustic wave that occurred between a subject and a subject holding member is suppressed.

In order to achieve the above-mentioned aim, a biological information acquisition apparatus according to an aspect of the present invention includes the following: a probe having a plurality of transformation elements that receive an acoustic wave emitted from a subject and that convert the acoustic wave into electric signals; a subject holding member provided between the subject and the probe; and a processing section configured to acquire image information using the electric signals. The processing section determines weights for the electric signals or virtual wavefronts corresponding to the electric signals to be added to one another, the weights being determined at least using a thickness of the subject holding member, a sound velocity of a sound propagating through the subject, a sound velocity of a sound propagating through the subject holding member, and arrival times of the acoustic wave from an acoustic-wave generating source in the subject, each of the electric signals or each of the virtual wavefronts being obtained by a corresponding one of the plurality of transformation elements. The processing section adds the weighted electric signals or the weighted virtual wavefronts to one another, thereby acquiring the image information.

Furthermore, a biological information acquisition method according to another aspect of the present invention includes the following: receiving, with each of transformation elements, an acoustic wave via a subject holding member and converting the acoustic wave into a corresponding one of electric signals, the acoustic wave being emitted from a subject; and acquiring image information from the electric signals. Arrival times of the acoustic wave from an acoustic-wave generating source are calculated in accordance with Snell's law at least using a thickness of the subject holding member, a sound velocity of a sound propagating through the subject holding member, a sound velocity of a sound propagating through the subject, and positions of image elements for the image information. The arrival times of the acoustic wave are corrected, thereby determining weights for the electric signals to be added to one another, each of the electric signals being obtained by a corresponding one of the transformation elements. The weighted electric signals are added to one another, thereby acquiring the image information.

A biological information acquisition method according to another aspect of the present invention includes the following: receiving, with each of transformation elements, an acoustic wave via a subject holding member and converting the acoustic wave into a corresponding one of electric signals, the acoustic wave being emitted from a subject; and acquiring image information from the electric signals. Virtual wavefronts of the acoustic wave are calculated in accordance with Snell's law at least using a thickness of the subject holding member, a sound velocity of a sound propagating through the subject holding member, a sound velocity of a sound propagating through the subject, and arrival times of the acoustic wave from an acoustic-wave generating source, each of the virtual wavefronts being calculated for a corresponding one of the transformation elements. Different levels are assigned to points constituting each of the virtual wavefronts using angles with respect to a corresponding one of the transformation elements as variables, thereby determining weights for the virtual wavefronts to be added to one another, the different levels corresponding to degrees of density. The weighted virtual wavefronts are added to one another, thereby acquiring the image information.

A biological information acquisition method according to another aspect of the present invention includes the following: receiving, with each of transformation elements, an acoustic wave via a subject holding member and converting the acoustic wave into a corresponding one of electric signals, the acoustic wave being emitted from a subject; and acquiring image information from the electric signals. Delay times for processing using a delay-and-sum are calculated in accordance with Snell's law at least using a thickness of the subject holding member, a sound velocity of a sound propagating through the subject holding member, a sound velocity of a sound propagating through the subject, and positions of image elements for the image information. A window function is corrected, thereby determining weights for the electric signals to be subjected to processing using the delay-and-sum, each of the electric signals being obtained by a corresponding one of the transformation elements. The weighted electric signals are subjected to processing using the delay-and-sum, thereby acquiring the image information.

According to the aspects of the present invention, not only the electric signals or the virtual wavefronts corresponding to the electric signals are added to one another in consideration of refraction of an acoustic wave that occurred between the subject and the subject holding member, but also the refraction can be considered in weighting for the electric signals or the virtual wavefronts to be added to one another. Thus, resolution can be improved.

DESCRIPTION OF EMBODIMENTS

Figure 1:
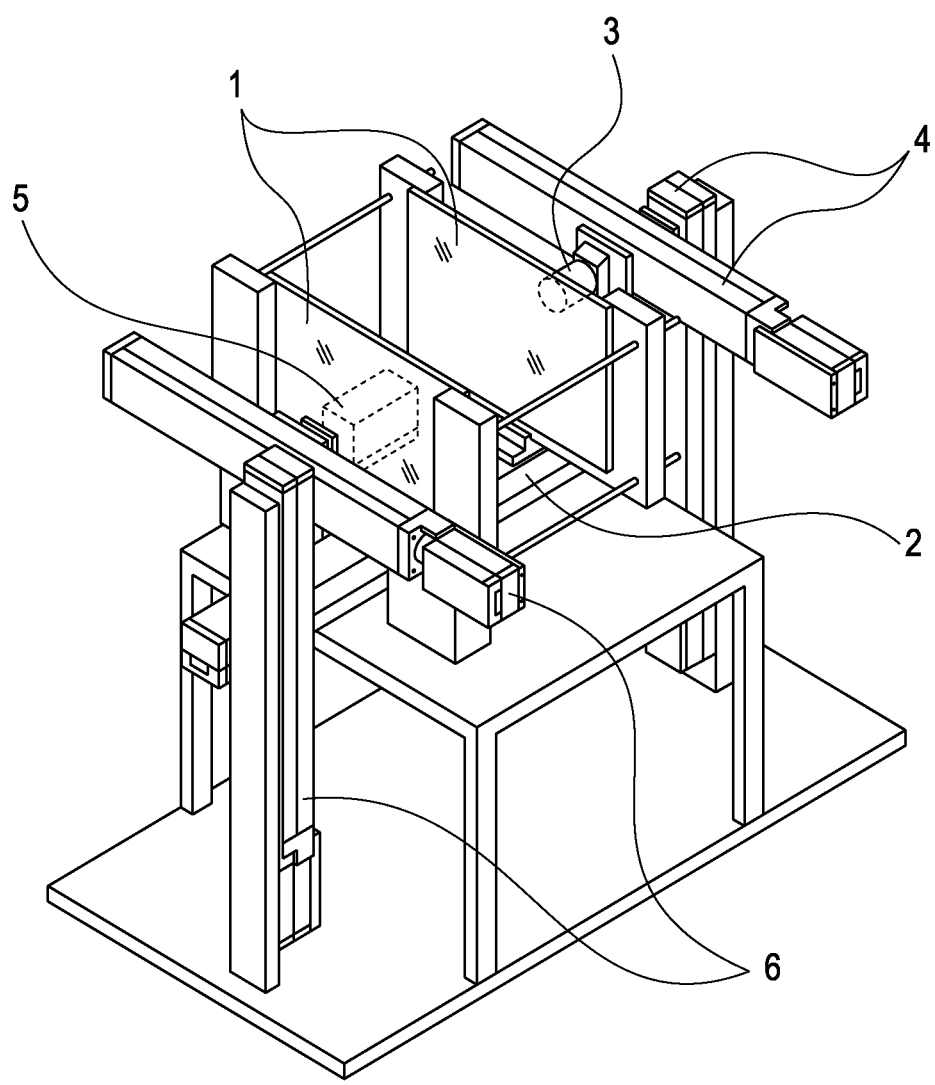
FIG. 1 is a diagram for explaining a system configuration of a photoacoustic mammography apparatus according to a first embodiment of the present invention.

A subject holding member is provided between a subject and a probe. The probe has a plurality of transformation elements that receive an acoustic wave and that convert the acoustic wave into signals (electric signals). In this case, refraction of the acoustic wave can be geometrically determined in accordance with Snell's law using a thickness of the subject holding member, a sound velocity of a sound propagating through the subject holding member, and a sound velocity of a sound propagating through the subject. Then, weights are determined for signals or virtual wavefronts corresponding to the signals to be added to one another. The weights are determined using positions of image elements (pixels or voxels) for image information, or using arrival times of the acoustic wave from an object that is an acoustic-wave generating source in the subject. The weighted electric signals or the weighted virtual wavefronts corresponding to the electric signals are added to one another, thereby acquiring the image information.

Note that examples of an acoustic wave in embodiments of the present invention include a wave called a sound wave, a wave called an ultrasound wave, and a wave called a photoacoustic wave. For example, the examples of an acoustic wave include a photoacoustic wave that is generated inside a subject by irradiating the inside of the subject with light such as near-infrared light, and an ultrasound wave that is transmitted to the inside of a subject and that is reflected. Furthermore, the examples of an acoustic wave emitted from a subject include an acoustic wave that is reflected by at least one portion of the subject, and an acoustic wave that is generated by the portion of the subject. In other words, examples of biological information acquisition apparatuses according to the embodiments of the present invention include the following apparatuses: a photoacoustic apparatus that irradiates the inside of a subject with light, that receives, using a probe, a photoacoustic wave which is generated inside the subject, and that displays an image of tissue of the inside of the subject; and an ultrasound apparatus that transmits/receives an ultrasound wave to/from the inside of a subject, and that displays an image of tissue of the inside of the subject. A subject holding member is provided between a subject and a probe, and holds the shape of at least one portion of the subject. Examples of the subject holding member include a member called a compression plate, a member called a parallel flat plate, and a member called a plate. The surface of the subject holding member may have a curvature.

Hereinafter, the embodiments of the present invention will be described. Note that, in the first and second embodiments, a biological information acquisition method and a photoacoustic mammography (hereinafter, referred to as "PAM") apparatus in which refraction of a photoacoustic wave is considered will be described. The biological information acquisition method and the PAM apparatus are PAMs using a photoacoustic tomography (hereinafter, referred to as "PAT") as a principle. More particularly, in the first embodiment, an image reconstruction method and a PAM apparatus in which refraction of a photoacoustic wave is considered using the delay-and-sum will be described. In the second embodiment, an image reconstruction method in which refraction of a photoacoustic wave is considered using the circular-back-projection will be described. In the third embodiment, a biological information acquisition method in which refraction of an ultrasound wave in an ultrasound apparatus is considered will be described.

EMBODIMENTS

First Embodiment

FIG. 1 is a schematic diagram of a configuration of a PAM apparatus. Using photoacoustic waves, because an image of blood or blood vessels can be distinctively acquired, an image of cancer angiogenesis can be picked up. FIG. 1 shows the configuration in which this principle is applied to breast cancer screening.

Referring to FIG. 1, plates 1 are parallel flat plates used as subject holding members in the first embodiment of the present invention. A compression mechanism 2 drives the two plates 1 so as to relatively move the plates 1 toward or away from each other. The plates 1 and the compression mechanism 2 are used to insert the subject (a breast) between the plates 1, and to press the subject. Note that, although a robot mechanism that performs automatic compression is illustrated as the compression mechanism 2, the compression mechanism 2 is not limited thereto. The compression mechanism 2 may be an air cylinder mechanism, a vise mechanism, or compression may be manually performed using a rack and pinion, worm gears, and so forth.

An illumination optical system 3 is an optical system for irradiating the subject with laser light having a wavelength that is approximately in the range of 700 nm to 1100 nm in order to cause the subject to generate a photoacoustic wave. Note that a propagation path of illumination light from a laser light source to the illumination optical system 3 is not illustrated. An illumination-light scan section 4 causes the illumination optical system 3 to perform scanning. A probe 5 is an acoustic-wave transducer that receives a photoacoustic wave which is generated by the subject. A probe scan section 6 causes the probe 5 to perform scanning.

A translucent resin, such as an acrylic resin or a polycarbonate resin, or an inorganic material, such as a quartz glass, is suitable as the material of the plate 1 at the side of the illumination optical system 3, which is one of the plates 1. In order to perform acoustic impedance matching in a path from the subject to the probe 5, a resin is suitable as the material of the plate 1 used as a subject holding member at the side of the probe 5, which is the other one. More particularly, polymethylpentene is suitable.

Next, a configuration will be described, in which a process sequence from reception of a photoacoustic wave with the probe 5 to performance of image reconstruction is realized.

Figure 2A:
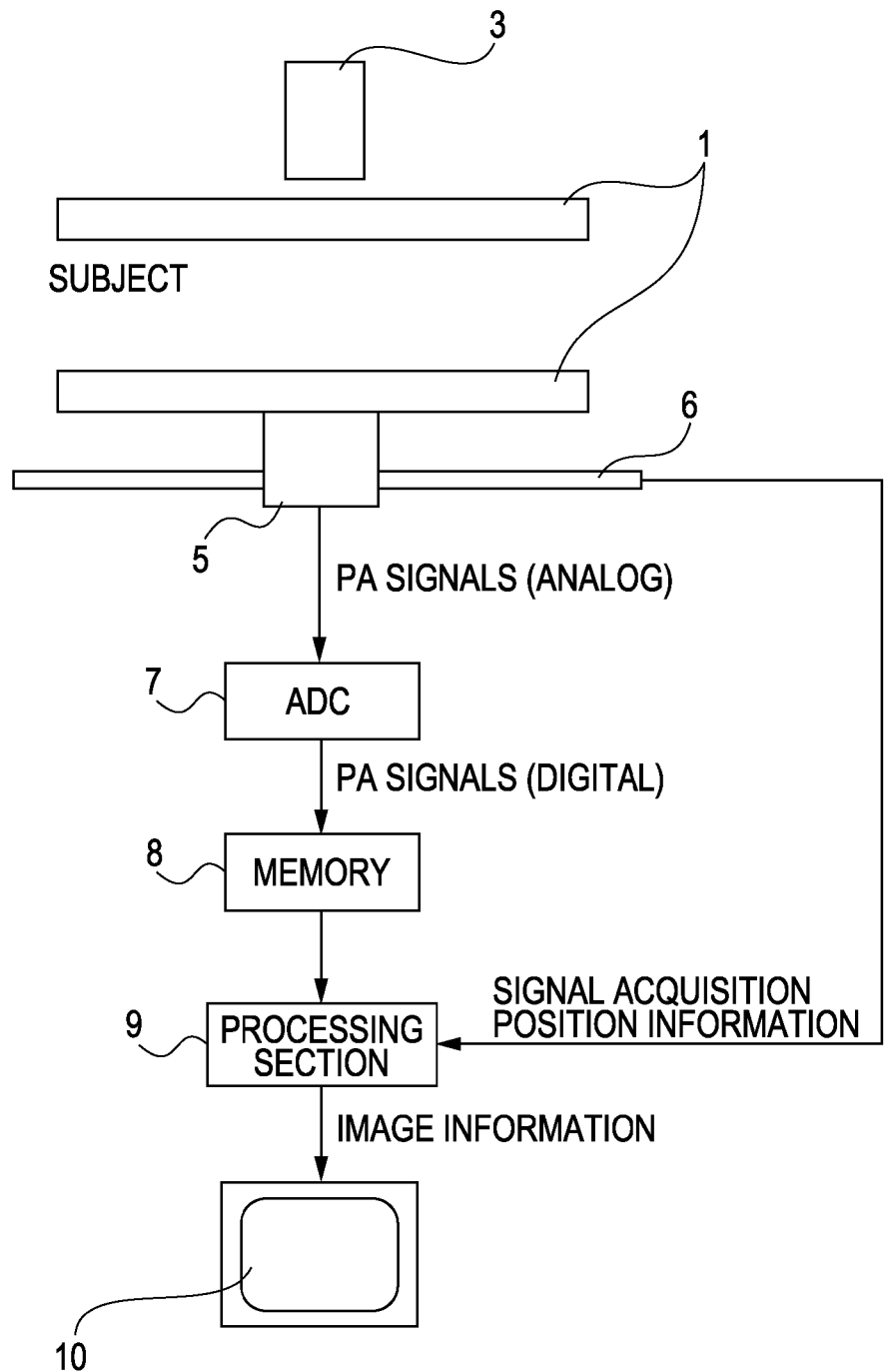
FIG. 2A is a diagram for explaining a signal processing section in the first embodiment of the present invention.

FIG. 2A is a diagram illustrating a signal flow of the process sequence from detection of a photoacoustic wave with the probe 5 to imaging of biological information concerning the subject using the photoacoustic wave. Referring to FIG. 2A, an analog-to-digital converter (ADC) 7 digitizes analog signals that the probe 5 has received, thereby obtaining digital signals. Note that, preferably, an amplifier for amplifying signals is provided between the probe 5 and the ADC 7. For example, the amplifier may be embedded in the probe 5. A memory 8 is a section that temporarily stores the digital signals. A processing section 9 performs a filtering process for noise reduction, and performs image reconstruction in accordance with signal acquisition position information that is supplied from the probe scan section 6. A display section 10 displays image information that is acquired by image reconstruction performed by the processing section 9.

Figure 2B:
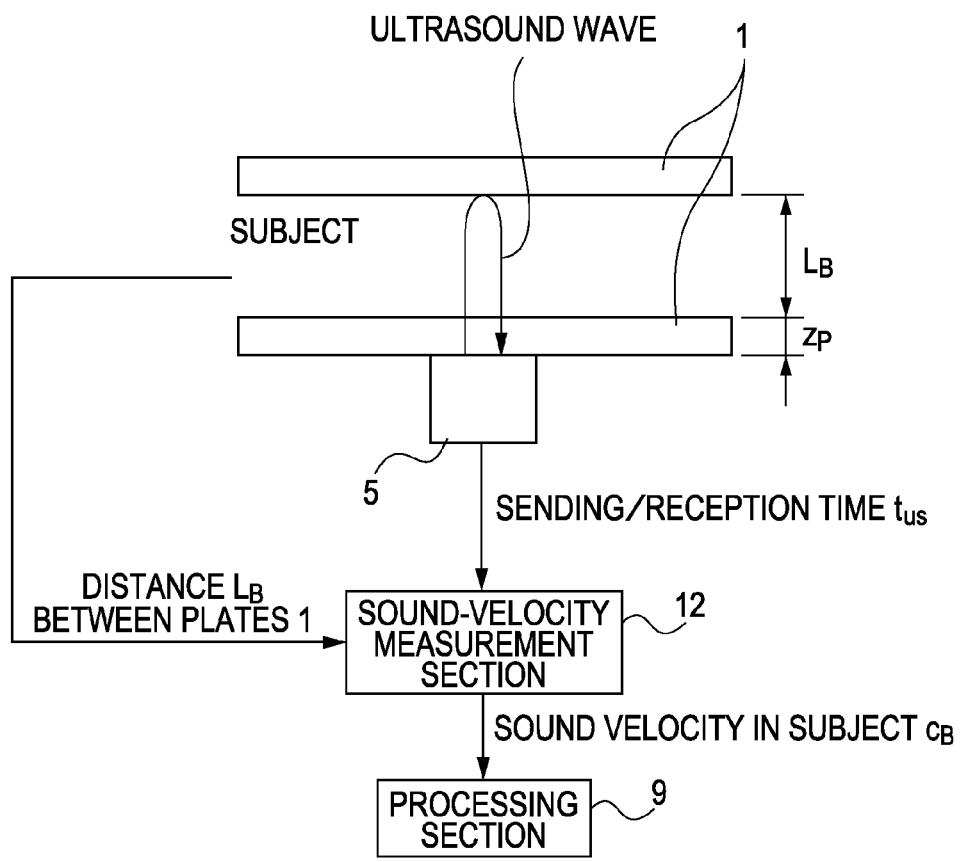
FIG. 2B is a diagram for explaining the signal processing section in the first embodiment of the present invention.

In the PAM apparatus that is described with reference to FIG. 1 and FIG. 2A, a sound velocity of a sound propagating through the subject is different from a sound velocity of a sound propagating through the plate. Accordingly, the photoacoustic wave is refracted at an interface between the subject and the plate. For example, the sound velocity in the subject is about 1540 m/s (about 1510 m/s in a breast). When the material of the plate 1 is polymethylpentene, the sound velocity in the plate 1 is about 2200 m/s. The numerical value given above can be used as the sound velocity in the subject. However, preferably, a sound velocity is measured by a sound-velocity measurement section 12 in advance, and the measured sound velocity is used when a correction table or a correction formula, which are described below, is determined. As shown in FIG. 2B, the sound-velocity measurement section 12 can measure the sound velocity in the subject using a method for, for example, calculating a sound velocity using a time $t_{us}$, which is a time from when an ultrasound wave is transmitted from the probe 5 to the subject sandwiched between the plates 1 to when the reflected ultrasound wave is received, and using a distance $L_B$ between the two plates 1. Note that, in a case of FIG. 2B, a sound velocity $c_B$ in the subject can be calculated using $c_B = L_B/(t_{us}/2 - z_p/c_p)$ because a thickness $z_p$ of the plate 1 and a sound velocity $c_p$ in the plate 1 are known.

Figure 3A:
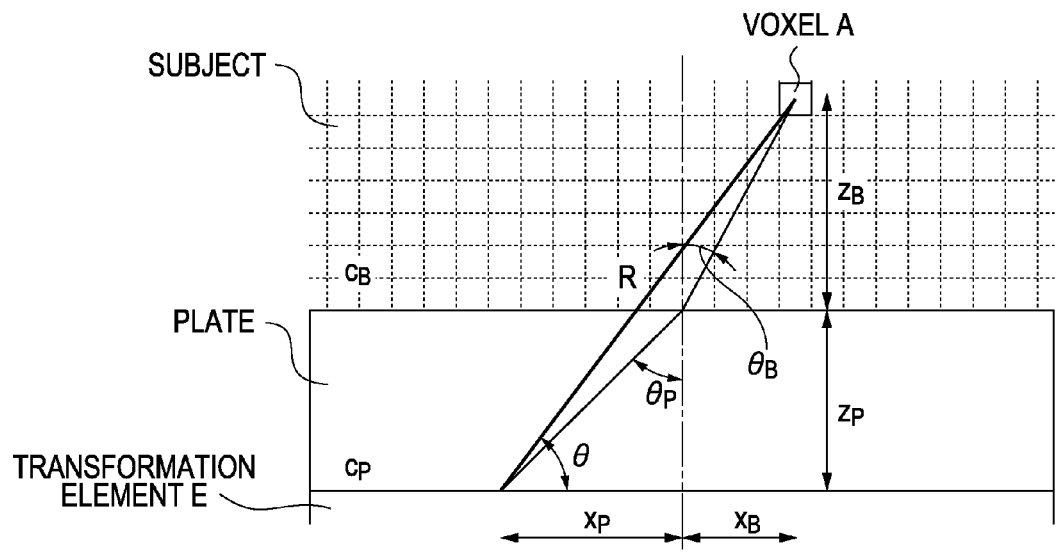
FIG. 3A is a diagram for explaining correction for refraction in the first embodiment of the present invention.
Figure 3B:
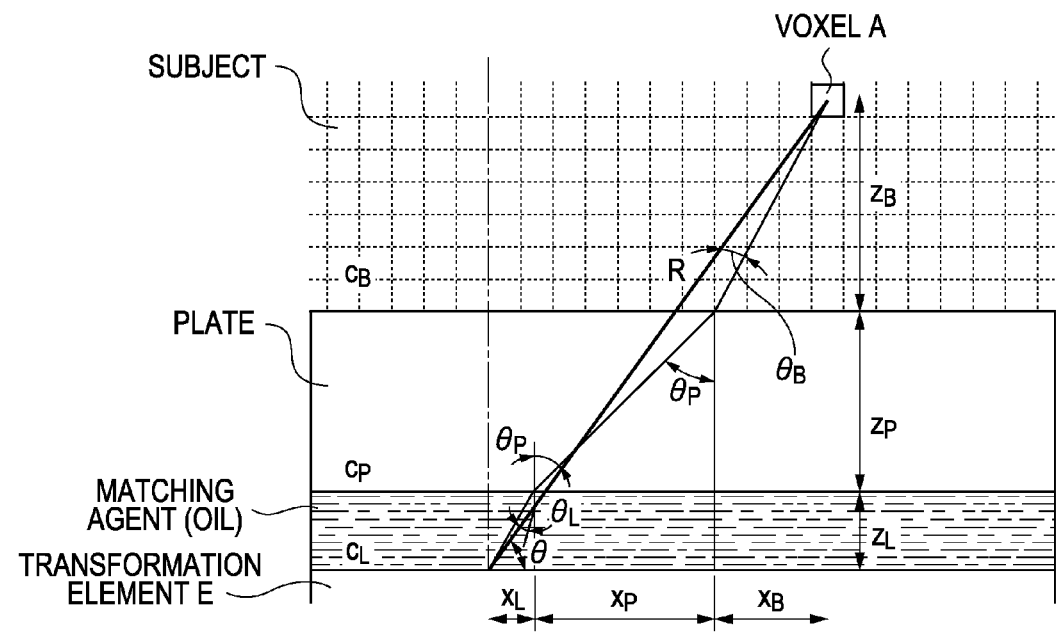
FIG. 3B is a diagram for explaining correction for refraction in the first embodiment of the present invention.

FIGS. 3A and 3B illustrate states in which a photoacoustic wave that is an acoustic wave is refracted. In the present invention, an image element is a pixel or voxel. Note that, for simplicity of description, states in two dimensions are described with reference to FIGS. 3A and 3B and the following drawings. However, the dimensions are not limited to two dimensions. The dimensions can be extended to three dimensions. Accordingly, in the description given below, an "image element" is denoted by a "voxel".

In image reconstruction using the delay-and-sum of the related art, in order to perform image reconstruction, voxels are defined, and calculation is performed for each of the voxels. For the image reconstruction, a relationship among an arrival time τ, which is to be calculated, taken for a photoacoustic wave to propagate from a voxel A to a transformation element E, a linear distance R between the voxel A and the transformation element E, and a sound velocity c is calculated in accordance with Equation (1), and imaging is performed. However, the sound velocity of a sound propagating through the subject is different from the sound velocity of a sound propagating through the plate. Accordingly, the photoacoustic wave is refracted at the interface between the subject and the plate, and the average sound velocity changes in accordance with θ and R. Thus, the sound velocity c is represented by a function using θ and R, and the arrival time τ can be represented by Equation (2).

$$\tau = \frac{R}{c} \quad (1)$$

$$\tau = \frac{R}{c(\theta, R)} \quad (2)$$

Furthermore, with reference to a path of the photoacoustic wave shown in FIG. 3A, Equation (2) for the arrival time $\tau$ can be derived by using Equation (3).

$$\tau = \frac{z_B}{c_B} \frac{1}{\cos\theta_B} + \frac{z_P}{c_P} \frac{1}{\cos\theta_P} \quad (3)$$

Moreover, referring to FIG. 3A, Equations (4) to (7) are provided as geometric equations.

$$\frac{c_B}{c_P} = \frac{\sin\theta_B}{\sin\theta_P} \quad (4)$$

$$\theta_P = \tan^{-1}\frac{x_P}{z_P} \quad (5)$$

$$\theta_B = \tan^{-1}\frac{x_B}{z_P} \quad (6)$$

$$x_P + x_B = R\cos\theta \quad (7)$$

Here, the sound velocity $c_B$ in the subject, the sound velocity $c_p$ in the plate, and the thickness $z_p$ of the plate are known. Furthermore, because the position of the voxel A, which is to be calculated, is known, a depth $z_B$ to the voxel A in the subject, the distance R from the voxel A to the transformation element E, and an angle $\theta$ are also known. Accordingly, a ratio of $x_p$ to $x_B$ is unknown. In other words, each of the values of $x_p$ and $x_B$ is unknown. That is, $x_p$ and $x_B$ can be calculated by substituting Equations (5) and (6) into Equation (4), and by solving Equations (4) and (7) as simultaneous equations. Furthermore, when $x_p$ and $x_B$ are determined by calculation, $\theta_p$ and $\theta_B$ can also be determined. Using the known values and the values determined by calculation, which are described above, the arrival time $\tau$ can be determined in accordance with Equation (3). Then, with reference to signals in the memory 8, whether or not there was a photoacoustic wave that had been generated by the subject and that arrived at the transformation element E at the arrival time $\tau$. For example, in the relationship between the transformation element E and the voxel A, when there was a photoacoustic wave that had been generated by the subject and that arrived at the transformation element E at the arrival time $\tau$, it can be determined that an acoustic-wave generating source, i.e., an illumination-light absorber (for example, new blood vessels), exists in the voxel A. Accordingly, image reconstruction is performed by performing processing using the delay-and-sum on signals acquired by individual transformation elements for each of the voxels, whereby a high-contrast image of the illumination-light absorber can be acquired. Because times at which the individual transformation elements receive the same photoacoustic wave are different from one another in accordance with the positions of the transformation elements, processing using the delay-and-sum is addition of signals to one another after the signals are corrected by only the different times (delay times).

Note that, as described above, resolution is improved by performing correction for at least refraction that occurred at the interface between the subject and the plate 1. However, there is a case in which an acoustic matching agent, such as water or oil, is provided between the plate 1 and the probe 5 as shown in FIG. 3B. Furthermore, there is also a case in which an acoustic matching agent, such as a sonar gel, is provided between the plate 1 and the subject. Although the sound velocities in these acoustic matching agents are close to the sound velocity in the subject, preferably, correction is also performed for refractions that occurred at interfaces associated with the acoustic matching agents. More particularly, preferably, correction is performed for refraction caused by the acoustic matching agent that is provided between the plate 1 and the probe 5. Even in this case, an influence caused by refraction can be geometrically determined as follows. Referring to FIG. 3B, Equation (3) corresponds to $\tau = \tau_L + \tau_P + \tau_B$. $\tau_L$ is a propagation time taken for a photoacoustic wave to propagate through the acoustic matching agent, and is represented by $\tau_L = z_L/(c_L \cos\theta_L)$. Similarly, $\tau_P$ is a propagation time taken for a photoacoustic wave to propagate through the plate 1, and is represented by $\tau_P = z_P/(c_P \cos\theta_P)$. $\tau_B$ is a propagation time taken for a photoacoustic wave to propagate through the subject, and is represented by $\tau_B = z_B/(c_B \cos\theta_B)$. Furthermore, Equation (4) corresponds to $\sin\theta_B/\sin\theta_P = c_B/c_P$ and $\sin\theta_P/\sin\theta_L = c_P/c_L$. Moreover, Equations (5) and (6) correspond to $\theta_B = \tan^{-1}(x_B/z_B)$, $\theta_P = \tan^{-1}(x_P/z_P)$, and $\theta_L = \tan^{-1}(x_L/z_L)$. Equation (7) corresponds to $x_L + x_P + x_B = R\cos\theta$.

Here, the sound velocity $c_B$ in the subject, the sound velocity $c_P$ in plate 1, and a sound velocity $c_L$ in the acoustic matching agent are known. The thickness $z_P$ of the plate and a thickness $z_L$ of the acoustic matching agent are also known. Furthermore, because the position of the voxel, which is to be calculated, is known, the depth $z_B$ to the voxel A in the subject, the distance R from the voxel A to the transformation element E, and the angle $\theta$ are also known. Accordingly, $x_L$, $x_P$, and $x_B$ that are unknown quantities can be determined using the above-mentioned equations as simultaneous equations. As described above, even when the number of interfaces at which refraction occurs is increased, the amounts of correction can be geometrically determined. However, in the following description, a refraction that occurred between the subject and the plate 1 is described. The refraction is a refraction, from among refractions that result in a reduction in resolution, for which an effect of correction is the largest. Description regarding refraction caused by the acoustic matching agent which is provided between the plate 1 and the probe 5 or between the plate 1 and the subject is omitted.

Next, the apodization technique (weighting) in a case of processing using the delay-and-sum will be described.

Figure 4:
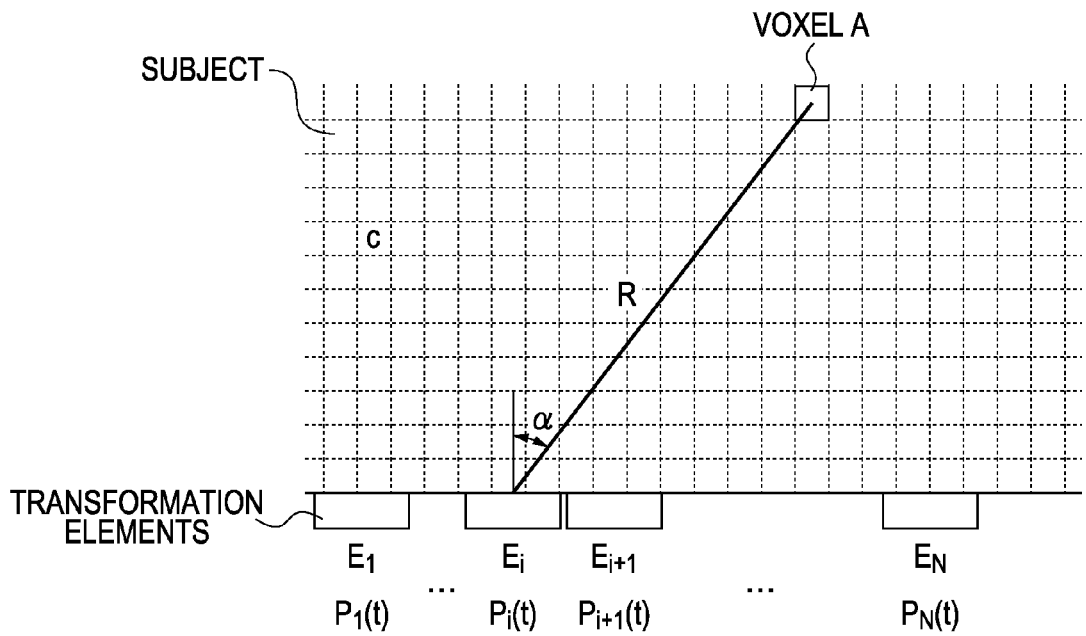
FIG. 4 is a diagram for explaining solid-angle correction in the first embodiment of the present invention.

In a case of processing using the delay-and-sum in the PAT, as shown in FIG. 4, correction using the apodization technique can be performed so that a solid angle correction (a solid angle weighting factor) is considered. When each of the transformation elements acquires a signal by receiving a photoacoustic wave, the intensity of the acquired signal differs depending on the position of the transformation element with respect to a position at which the photoacoustic wave is generated. Thus, solid angle correction in this case is correction of the differences among the intensities of the acquired signals. An equation for the delay-and-sum in a case in which correction using the apodization technique is performed is derived by using Equations (8) and (9).

$$S(r) = \int_{\Omega_0} b_i(t - \tau_i) \frac{d\Omega_0}{\Omega_0} \quad (8)$$

-continued $$b(r) = 2P_i(t) - 2 \cdot t \cdot \frac{\partial P_i(t)}{\partial t} \quad (9)$$

Here, t is a time, and τ is the arrival time that is determined using Equations (3) to (7) described above. $P_i$ is an acquired signal that is stored in the memory 8, and $\Omega_0$ denotes a region bordered using a detector (the probe 5) (a region that is detected). As shown in FIG. 1, since the probe 5 scans the flat plate 1, the equation for the delay-and-sum can be derived by using Equation (10). Note that $A_0$ denotes a transformation element area.

$$S(r) \cong \frac{\sum_{i=1}^{N} b_i(t - \tau_i) \cdot \frac{A_0}{R_i^2} \cos\alpha_i}{\sum_{i=1}^{N} \frac{A_0}{R_i^2} \cos\alpha_i} \quad (10)$$

Figure 5:
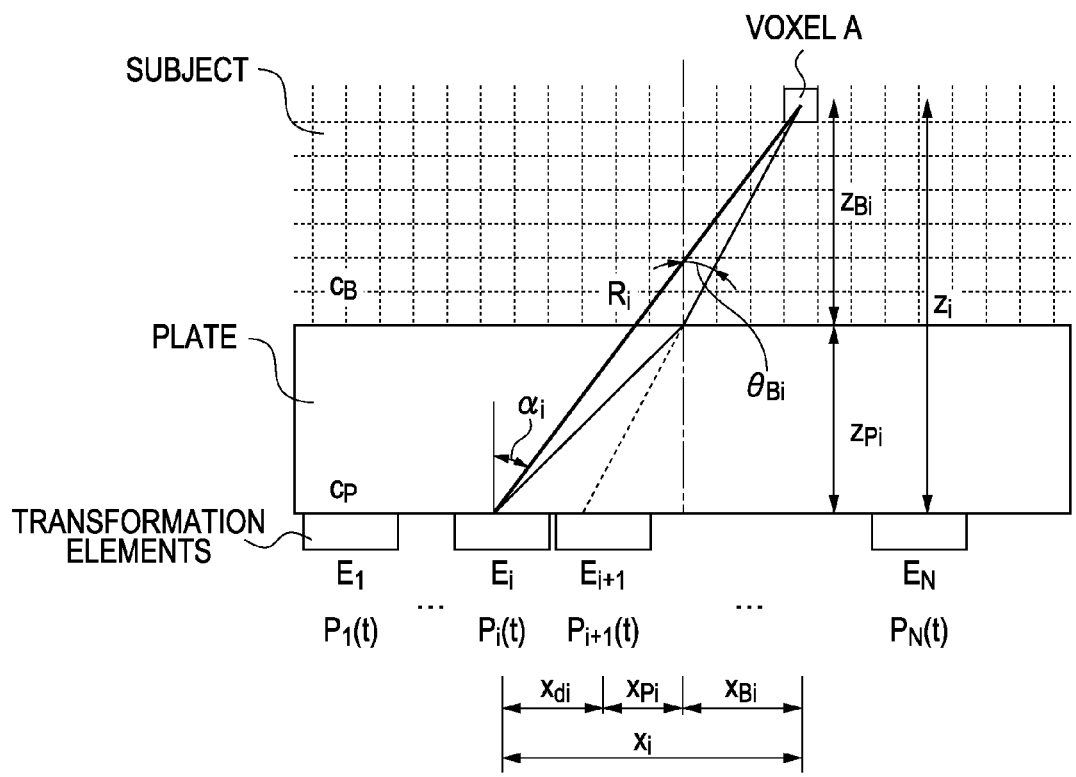
FIG. 5 is a diagram for explaining the apodization technique in the first embodiment of the present invention.

In the PAM apparatus shown in FIG. 1, a photoacoustic wave is refracted by the plate 1. Accordingly, as shown in FIG. 5, a photoacoustic wave that is generated by the voxel A arrives at a transformation element $E_i$ although the photoacoustic wave should arrive at a transformation element $E_{i+1}$. In other words, supposing that a signal acquired by the transformation element $E_i$ is a signal which should have been acquired by the transformation element $E_{i+1}$, processing using the delay-and-sum can be performed. That is, the position at which the photoacoustic wave arrived can be corrected by a distance $x_{di}$ between the transformation element $E_i$ and the transformation element $E_{i+1}$ in Equation (10). Referring to FIG. 5, when it is supposed that the signal acquired by the transformation element $E_i$ is the signal which should have been acquired by the transformation element $E_{i+1}$, a linear distance $R_i$ and an angle $\alpha_i$ can be represented by Equation (11). Then, with Equation (10) into which Equation (11) is substituted, in a case of processing using the delay-and-sum, correction using the apodization technique in which refraction of the photoacoustic wave is considered can be performed.

$$\begin{cases} \alpha_i = \theta_{Bi} \\ R_i = \sqrt{(x_i - x_{di})^2 + z_i^2} \\ \quad = \sqrt{(x_{Pi} + x_{Bi})^2 + (z_{Pi} + z_{Bi})^2} \\ \quad = \sqrt{[(z_{Pi} + z_{Bi})\tan\theta_{Bi}]^2 + (z_{Pi} + z_{Bi})^2} \\ \quad = \frac{z_P + z_{Bi}}{\cos\theta_{Bi}} \text{ where } z_{Pi} = z_P \end{cases} \quad (11)$$

Note that, although the description above is made under the assumption that the plate 1 is a flat plate, the plate used as a subject holding member is not limited to a flat plate. Regarding the flatness of the plate, even when the surface of the plate has a curvature, the plate is effective. When the surface of the plate 1 has a curvature, preferably, an incident angle corresponding to the curvature reflects in $\theta_B$ and $\theta_P$. The equation for the delay-and-sum that is derived by using Equations (10) and (11), i.e., the equation for the delay-and-sum in a case in which correction using the apodization technique is performed, is established for a case in which the flat probe 5 is caused to perform scanning in the flat plate 1. When the plate 1 is not a flat plate, Equation (8) is expanded in accordance with a region of the surface to be measured, and equations corresponding to Equations (10) and (11) are derived, whereby correction can be performed for refraction of a photoacoustic wave.

Furthermore, the description with reference to FIG. 1 is made under the assumption that the plates 1 are two flat parallel plates. However, the above-described method for acquiring image information can be applied to a case in which one of the plates 1 is provided between the subject and the probe 5. The use of the plates 1 is not limited to compression of the subject.

As described above, image reconstruction can be performed in consideration of refraction that occurred due to the different between the sound velocity of a sound propagating through the subject and the sound velocity of a sound propagating through the plate 1. In a case of image reconstruction, not only refraction is considered in addition of signals to one another, but also the refraction can be considered in the apodization technique that is used in the addition of signals to one another. Thus, a reduction in resolution that is caused by refraction of a photoacoustic wave can be suppressed.

Second Embodiment

In the first embodiment, the method for performing correction for refraction of a photoacoustic wave in a case of image reconstruction using the delay-and-sum is described. However, the present invention is not limited to the method, and a method for performing correction using the circular-back-projection is also effective.

Figure 6A:
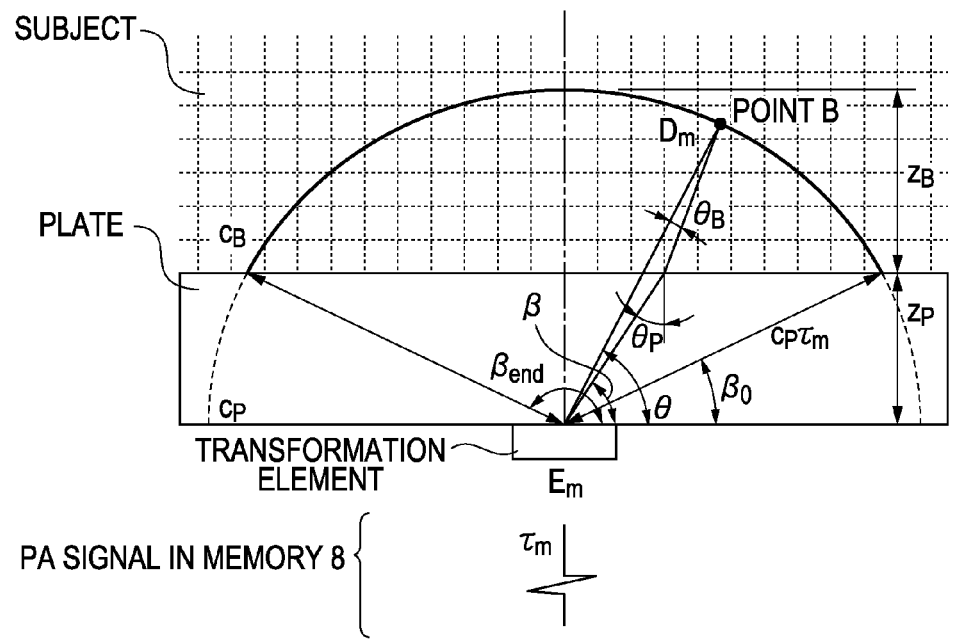
FIG. 6A is a diagram for explaining a method for calculating a position of a wavefront using a circular-back-projection in a second embodiment of the present invention.

FIG. 6A is a diagram for explaining a method for calculating a curve (a point B) using the circular-back-projection. Referring to FIG. 6A, a curve from $\beta_0 = \sin^{-1}(z_p/c_P\tau_m)$ to $\beta_{end} = \pi - \beta_0$ is determined. For example, when determination of the point B is performed, because $z_p$, which is the thickness of the plate 1, and $c_P$, which is the sound velocity in the plate 1, are known, a distance from a transformation element $E_m$ to the interface between the plate 1 and the subject can be determined. Accordingly, a propagation time $t_P$ taken for a photoacoustic wave to propagate through the distance can be calculated. An angle of refraction can be calculated in accordance with Snell's law represented by Equation (4). Because an arrival time of the photoacoustic wave that is determined using an acquired signal is $\tau_m$, a propagation time $t_B$ taken for the photoacoustic wave to propagate through the subject can be calculated using $t_B = \tau_m - t_P$. A point that is determined by extending a line from the interface between the plate 1 and the subject by $c_B \cdot L_B$ in a direction of the angle of refraction can be determined as the point B. Furthermore, when the point B is determined, an angle θ defined by a straight line from the point B to the transformation element $E_m$, and $D_m$ that is a distance from the transformation element $E_m$ to the point B can be calculated. In this manner, $D_m$ can be represented by a function using θ ($D_m(\theta)$), and a curve for the circular-back-projection, i.e., a virtual wavefront for each of the transformation elements, can be drawn.

Then, the arrival time τ is determined, for each of the transformation elements, using a signal that is stored in the memory 8 and that was acquired by receiving the photoacoustic wave, and a curve is drawn for each of the transformation elements as described above, whereby image reconstruction can be performed.

Figure 6B:
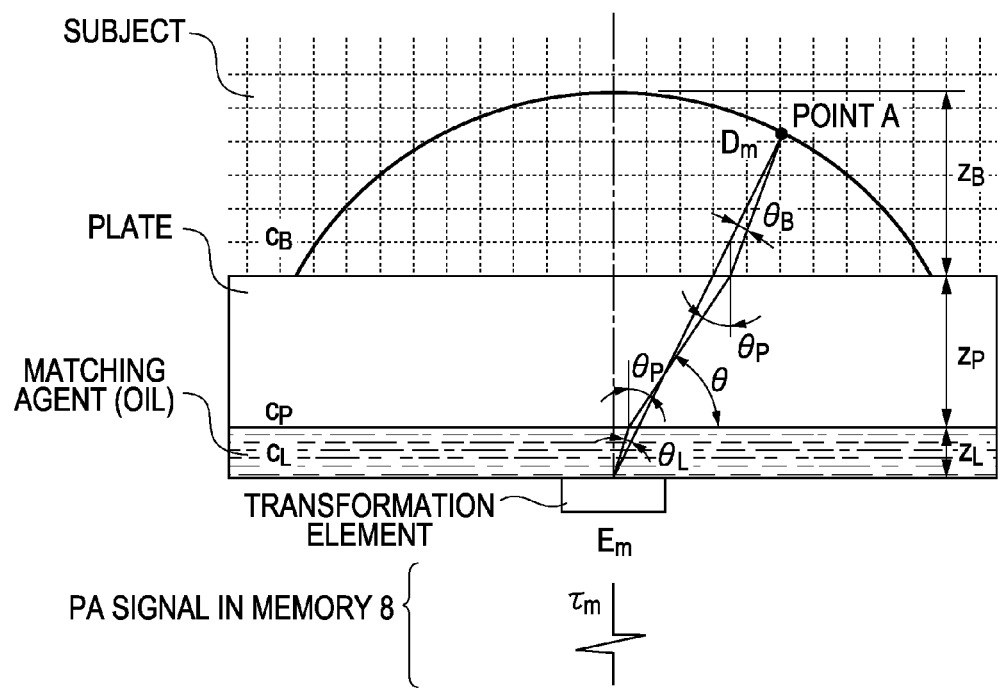
FIG. 6B is a diagram for explaining the method for calculating a position of a wavefront using the circular-back-projection in the second embodiment of the present invention.

Note that, as described with reference to FIG. 3B in the first embodiment, there is a case in which an acoustic matching agent, such as water or oil, exists between the plate 1 and the probe 5. Even when the number of interfaces at which refraction occurs is increased, the amounts of correction can be geometrically determined. For example, referring to FIG. 6B, $D_m$ given above can be calculated using $D_m(\theta)=((z_L \tan \theta_L + z_P \tan \theta_P + z_B \tan \theta_B)^2 + (Z_L + Z_P + Z_B)^2)^{1/2}$ and using $\tan \theta = (z_L + z_P + z_B)/(z_L \tan \theta_L + z_P \tan \theta_P + z_B \tan \theta_B)$. In other words, $D_m$ is represented by a function using $\theta$, and $\theta$ is represented by a function using $\theta_L$, $\theta_P$, and $\theta_B$ that are angles of refractions at individual interfaces. Regarding $\theta_L$, $\theta_P$, and $\theta_B$, equations therefor can be derived by using $\sin \theta_B/\sin \theta_P = c_B/c_P$ and $\sin \theta_P/\sin \theta_L = c_P/c_L$ in accordance with Snell's law. $z_L$ is a thickness of the acoustic matching agent, and $c_L$ is a sound velocity in the acoustic matching agent.

Furthermore, the arrival time of the photoacoustic wave $\tau_m$ is represented by $\tau_m = \tau_L + \tau_P + \tau_B$. $\tau_L$ is a propagation time taken for a photoacoustic wave to propagate through the acoustic matching agent, and is represented by $\tau_L = z_L/(c_L \cos \theta_L)$. Similarly, $\tau_P$ is a propagation time taken for a photoacoustic wave to propagate through the plate, and is represented by $\tau_P = z_P/(c_P \cos \theta_P)$. $\tau_B$ is a propagation time taken for a photoacoustic wave to propagate through the subject, and is represented by $\tau_B = z_B/(c_B \cos \tau_B)$. $D_m(\theta)$ can be calculated using these equations.

Figure 7:
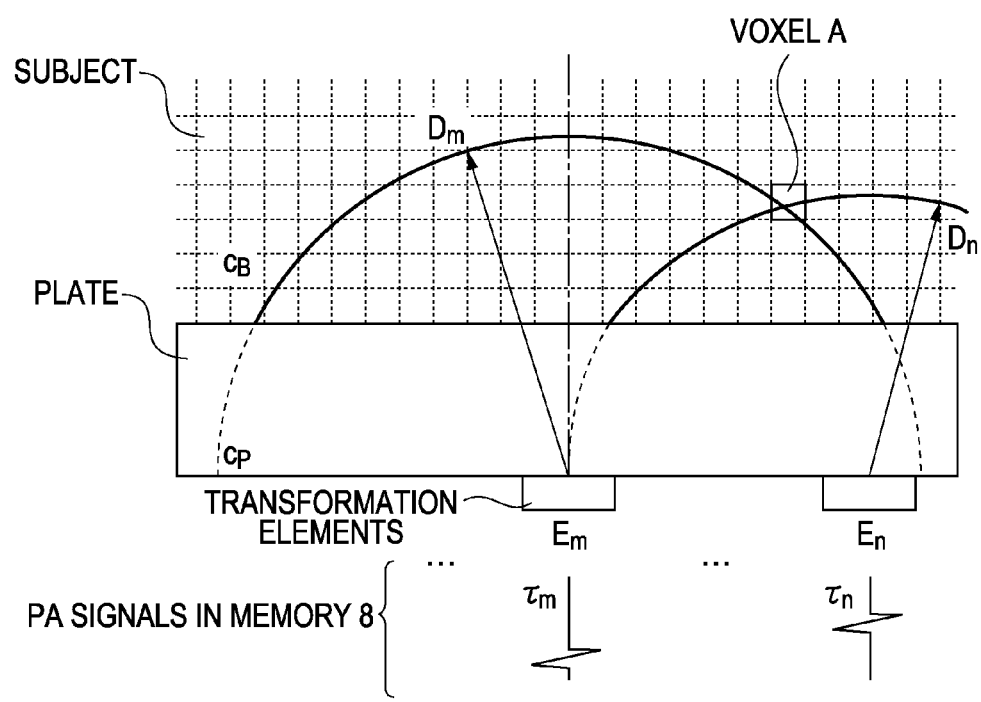
FIG. 7 is a diagram for explaining the circular-back-projection in the second embodiment of the present invention.

FIG. 7 is a schematic diagram, which is illustrated as an example, for performing image reconstruction using the transformation elements $E_m$ and $E_n$, and using the arrival times $\tau_m$ and $\tau_n$ at which the photoacoustic wave arrived at the transformation elements $E_m$ and $E_n$, respectively. As shown in FIG. 7, each of virtual wavefronts for the circular-back-projection is drawn for a corresponding one of the transformation elements. Considering a point at which the virtual wavefronts overlap each other (the voxel A) as a sound source of the photoacoustic wave, i.e., an illumination-light absorber, image reconstruction can be performed.

Weighting corresponding to the apodization technique is performed by assigning different levels to points constituting each of the virtual wavefronts for the circular-back-projection in accordance with the positions of the points. The different levels correspond to degrees of density. Referring to FIG. 6A, the highest level is assigned to an angle defined by a point that is positioned immediately above a corresponding transformation element, i.e., β of 90°. As β defined by a point decreases, the level that is to be assigned to the point is made lower. For example, weighting is performed by multiplying the highest level by values of cos β that are determined for the individual points, whereby different levels can be assigned to the points constituting the virtual wavefront. In this manner, different levels corresponding to degrees of density are assigned to the points constituting the virtual wavefront using, as variables, angles defined by the points with respect to the transformation element, whereby weights can be determined.

As described above, image reconstruction in consideration of refraction can be performed also using an algorithm (the circular-back-projection) other than the delay-and-sum that is described in the first embodiment. In such a case, not only refraction is considered for the virtual wavefronts corresponding the signals, but also the refraction can be considered in assignment of different levels, which correspond to degrees of density, to the points constituting the virtual wavefronts. Thus, a reduction in resolution that is caused by refraction of a photoacoustic wave can be suppressed.

Third Embodiment

The PAM apparatus that operates using the PAT as a principle is described in the first and second embodiments. In the third embodiment, a configuration of an ultrasound apparatus and a processing method in a case in which the PAT is applied to the ultrasound apparatus are described. Even in a case of an ultrasound apparatus that transmits/receives an ultrasound wave to/from a subject, when a plate is provided between an ultrasound probe and the subject, a transmitted ultrasound wave is refracted. A typical ultrasound apparatus does not transmit/receive an ultrasound wave via a plate to a subject. However, when an ultrasound probe is provided in parallel to the probe 5 of the PAM apparatus shown in FIG. 1, or when an ultrasound probe is provided on a compression plate of an X-ray mammography apparatus, it is necessary to consider refraction that occurs because of the difference between a sound velocity in the subject and a sound velocity in the plate. Supposing such a case, FIG. 8 is a diagram illustrating a signal flow of a process sequence from transmission of an ultrasound wave from an ultrasound probe toward a subject to reception of the ultrasound wave, which is reflected by the subject, and imaging.

Figure 8:
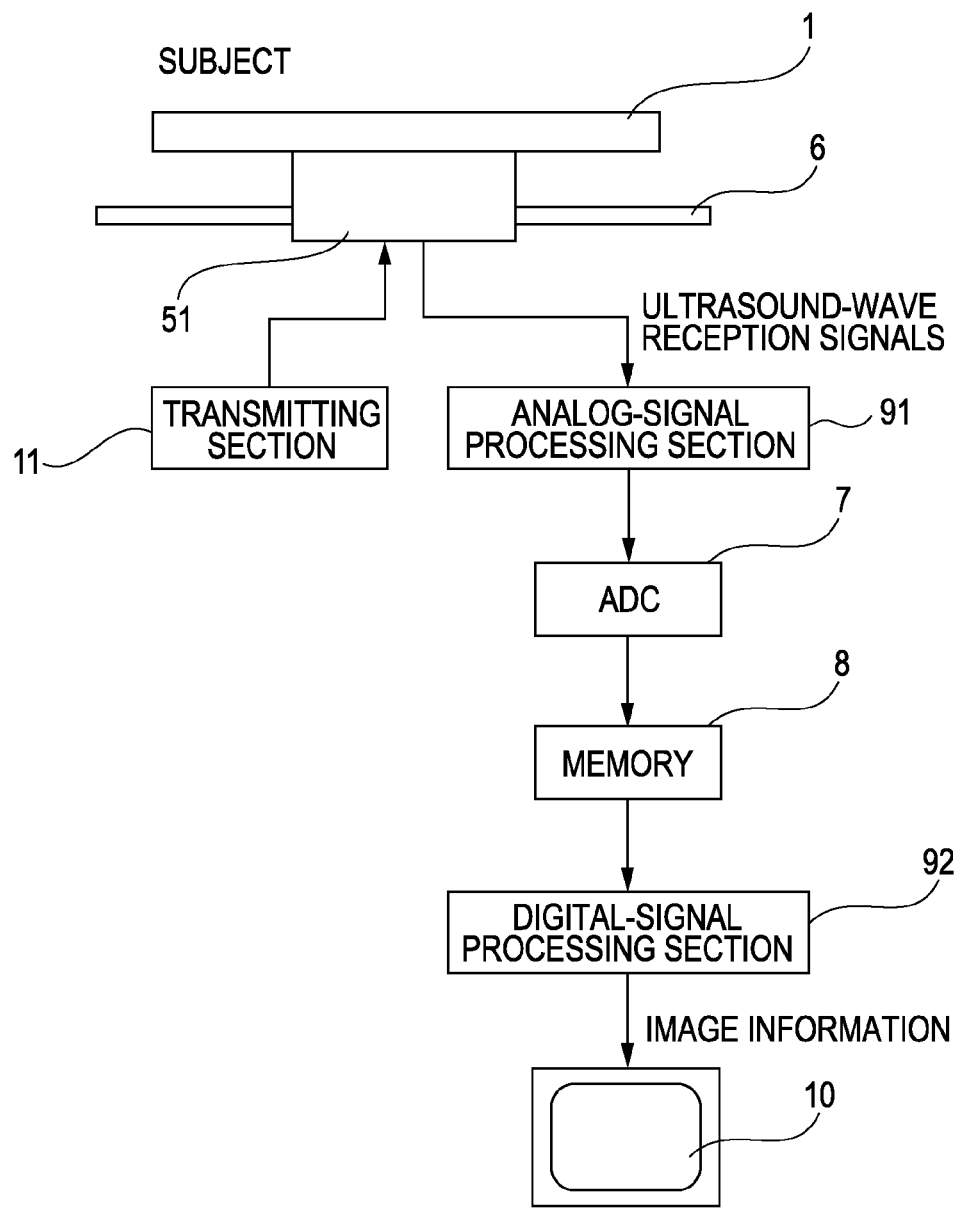
FIG. 8 is a diagram for explaining a signal processing section in a third embodiment of the present invention.

Referring to FIG. 8, a transmitting section 11 performs a process such as a transmission beamforming process for transmitting an ultrasound wave. An ultrasound probe 51 transmits/receives an ultrasound wave in accordance with a transmission signal from the transmitting section 11. An analog-signal processing section 91 performs a filtering process and an amplification process. The ADC 7 digitizes analog signals that have been subjected to signal processing by the analog-signal processing section 91, thereby obtaining digital signals. The memory 8 stores the digital signals (reception signals) as a time series. A digital-signal processing section 92 acquires image information using the reception signals stored in the memory 8, and causes the display section 10 to display the image information. In an ultrasound apparatus, the digital-signal processing section 92 performs a reception beamforming process on the reception signals stored in the memory 8, and the reception beamforming process includes detection of an ultrasound echo, processing using the delay-and-sum, and so forth. The digital-signal processing section 92 performs signal processing, such as compression using logarithm, and performs image processing. In this case, for delay times (the differences among arrival times at an ultrasound wave arrived at individual transformation elements) in a case of processing using the delay-and-sum, the digital-signal processing section 92 considers the sound velocity in the subject and the sound velocity in the plate 1. Similarly, for a transmission beamforming process, the transmitting section 11 determines delay times in consideration of the sound velocity in the subject and the sound velocity in the plate 1, and oscillates the ultrasound probe 51.

Figure 9:
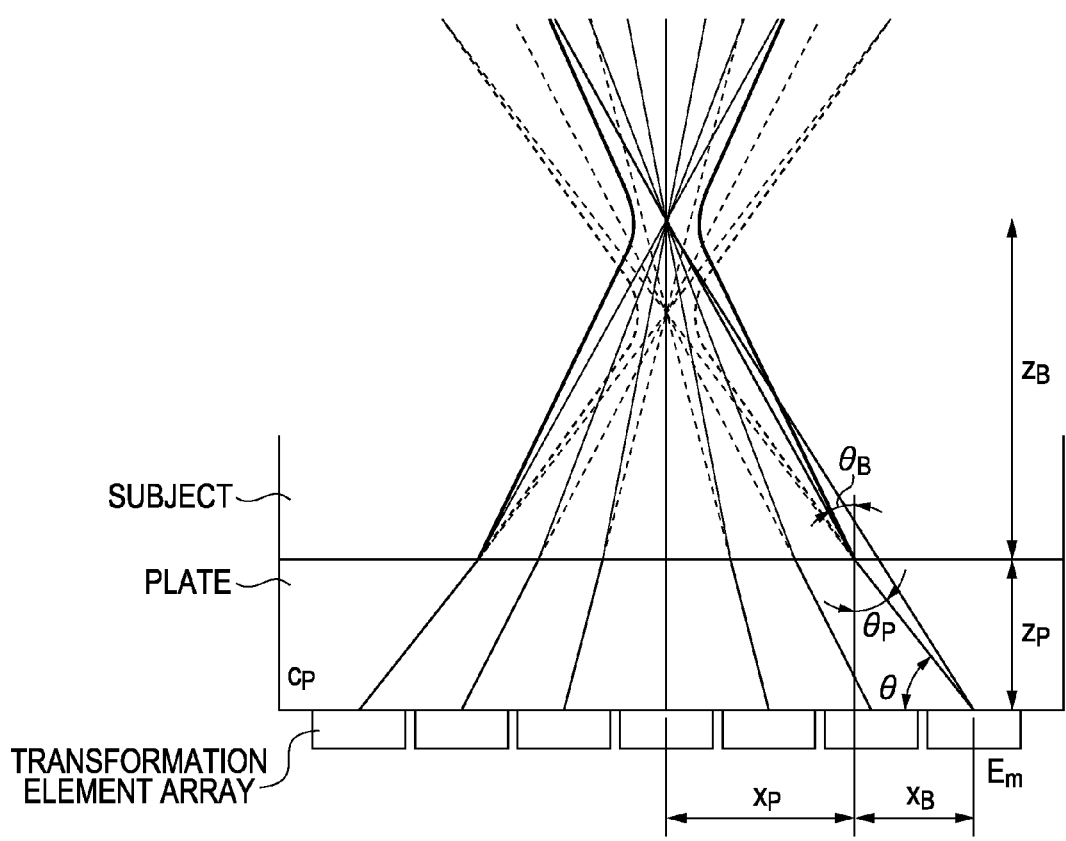
FIG. 9 is a diagram for explaining a beamforming process in the third embodiment of the present invention.

In each of the reception beamforming process performed by the digital-signal processing section 92 and the transmission beamforming process performed by the transmitting section 11, a difference between a result that was obtained in consideration of the difference between the sound velocity in the subject and the sound velocity in the plate and a result that was obtained without consideration of the difference between the sound velocity in the subject and the sound velocity in the plate occurs as shown in FIG. 9. In FIG. 9, the solid lines indicate the result that was obtained in consideration of the difference between the sound velocity in the subject and the sound velocity in the plate. The broken lines indicate the result that was obtained without consideration of the difference between the sound velocity in the subject and the sound velocity in the plate. Referring to FIG. 9, in order to determine a desired focus position, it is necessary to consider the difference between the sound velocity in the subject and the sound velocity in the plate 1. Accordingly, a method similar to the method that is described with reference to FIG. 3A can be used as a method for determining the delay times in each of the reception beamforming process and the transmission beamforming process.

The sound velocity $c_B$ in the subject, the sound velocity $c_p$ in the plate, and the thickness $z_p$ of the plate are known. Furthermore, a distance $z_B$ from the desired focus position to the plate 1, a distance R from the desired focus position to the transformation element E, and an angle θ are also known. Accordingly, a ratio of $x_p$ to $x_B$ is unknown. In other words, each of the values of $x_p$ and $x_B$ is unknown. That is, $x_p$ and $x_B$ can be calculated by substituting Equations (5) and (6) into Equation (4), and by solving Equations (4) and (7) as simultaneous equations. Furthermore, when $x_p$ and $x_B$ are determined by calculation, $\theta_p$ and $\theta_B$ can also be determined. Using the known values and the values determined by calculation, which are described above, a delay time is calculated for each of the transformation elements in accordance with Equation (3). Then, when the delay times are calculated for the individual transformation elements, a beamforming process is performed using the delay times. Note that, in the reception beamforming process, processing using the delay-and-sum is performed by performing correction using the apodization technique on a reception signal for each of the transformation elements. In correction using the apodization technique, a function that is generally called a window function is applied.

Note that, as in the case of the first embodiment, even in a case in which an acoustic matching agent, such as water or oil, exists between the plate 1 and the probe 5, the amounts of correction can be geometrically determined.

Figure 10:
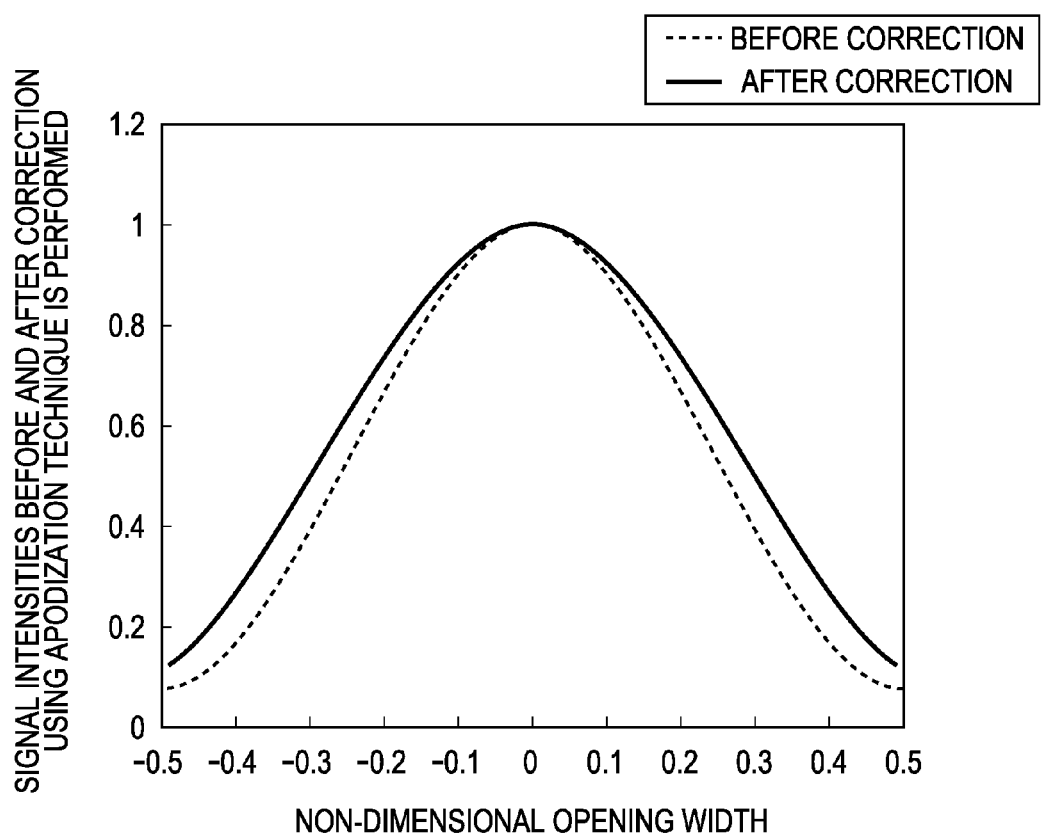
FIG. 10 is a diagram for explaining an apodization function in the third embodiment of the present invention.
Figure 11:
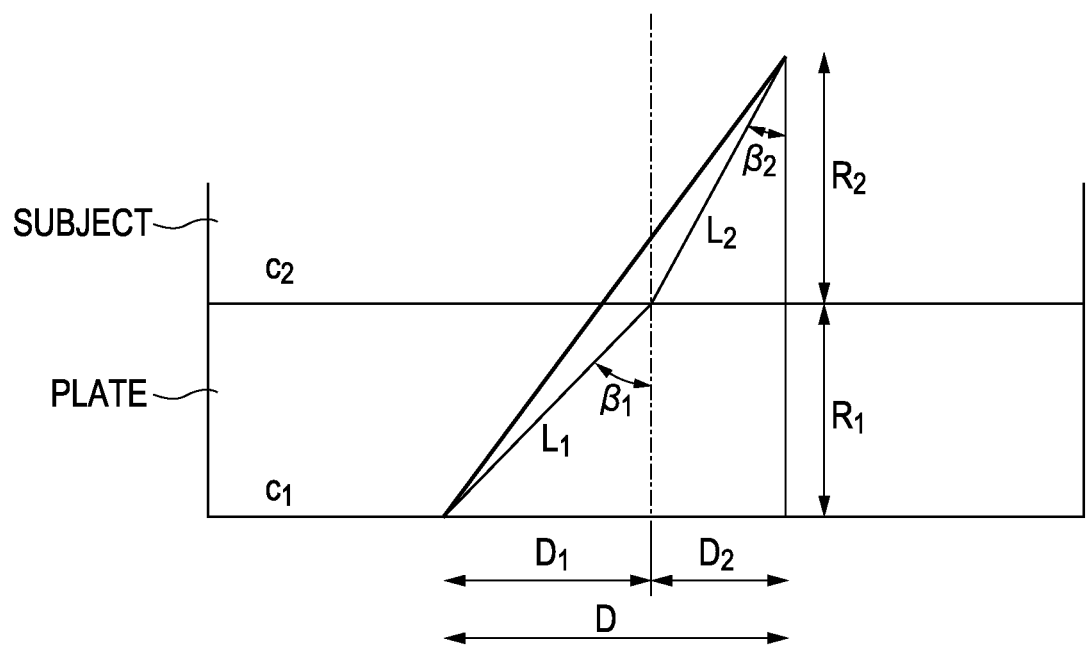
FIG. 11 is a diagram for explaining the background art.

A correction method using the apodization technique in a case in which a hamming window function is applied as one example of a window function is described. The hamming window function is represented by w(x)=0.54−0.46 cos (2πx). However, x is a non-dimensional opening width, and, in order to position the center of the opening width at zero, the above-mentioned equation is changed to w(x)=0.54−0.46 cos [2π(x−0.5)]. Furthermore, in correction using the apodization technique, with reference to FIG. 5, an apodization function is determined as w(x)=0.54−0.46 cos [2π($x_{di}$−0.5)]. $x_{di}$ can be geometrically determined using $\theta_B$ that has already be calculated when the delay times have been determined. In this manner, an apodization function can be determined. In order to compare signal intensity before correction using the apodization technique is performed (the dotted line) with signal intensity after correction using the apodization technique is performed (the solid line), FIG. 10 illustrates the apodization function when the hamming window function is applied as a window function.

In a case of the above-described apodization function, the hamming window function is used as a window function. However, the window function is not limited to the hamming window function. Also when a window function other than the hamming window function is used, an apodization function can be determined using a method that is the same as the above-described method.

As described above, image acquisition in consideration of refraction can be performed not only by the PAT (the PAT apparatus), which is described in the first and second embodiments, but also by the ultrasound apparatus. In a case in which the ultrasound apparatus is used, not only refraction can be considered in processing using the delay-and-sum is performed, but also the refraction can be considered in the apodization technique. Thus, a reduction in resolution that is caused by refraction of an ultrasound wave can be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A subject information acquisition apparatus comprising:
a subject holding member configured to hold a subject;
a probe having a plurality of transformation elements that receive an acoustic wave emitted from the subject through the subject holding member and that convert the acoustic wave into electric signals; and
a processing section configured to acquire image information using the electric signals,
wherein the processing section determines weights for the electric signals or virtual wavefronts corresponding to the electric signals to be added to one another, the weights being determined at least using a thickness of the subject holding member, a sound velocity of a sound propagating through the subject, a sound velocity of a sound propagating through the subject holding member, and arrival times of the acoustic wave from an acoustic-wave generating source in the subject, each of the electric signals or each of the virtual wavefronts being obtained by a corresponding one of the plurality of transformation elements, and
wherein the processing section adds the weighted electric signals or the weighted virtual wavefronts to one another, thereby acquiring the image information.

2. The subject information acquisition apparatus according to claim 1,
wherein the acoustic wave is a photoacoustic wave that is generated by the acoustic-wave generating source in the subject by irradiating the subject with light,
wherein the processing section determines weights for the electric signals or the virtual wavefronts corresponding to the electric signals to be added to one another, the weights being determined at least using the thickness of the subject holding member, the sound velocity of a sound propagating through the subject, the sound velocity of a sound propagating through the subject holding member, and arrival times of the photoacoustic wave from the acoustic-wave generating source in the subject, each of the electric signals or each of the virtual wavefronts being obtained by a corresponding one of the plurality of transformation elements, and
wherein the processing section adds the weighted electric signals or the weighted virtual wavefronts to one another, thereby acquiring the image information.

3. The subject information acquisition apparatus according to claim 1,
wherein the acoustic wave is an ultrasound wave that is transmitted to the subject, that is reflected by the acoustic-wave generating source, and that is returned,
wherein the processing section determines delay times for the electric signals to be subjected to processing using a delay-and-sum, the delay times being determined at least using the thickness of the subject holding member, the sound velocity of a sound propagating through the subject, the sound velocity of a sound propagating through the subject holding member, and positions of image elements for the image information, each of the electric signals being obtained by a corresponding one of the plurality of transformation elements, and
wherein the processing section performs processing using the delay-and-sum on the weighted electric signals, and adds the electric signals to one another, thereby acquiring the image information.

4. The subject information acquisition apparatus according to claim 1, wherein the processing section calculates the arrival times of the acoustic wave from the acoustic-wave generating source in accordance with Snell's law at least using the thickness of the subject holding member, the sound velocity of a sound propagating through the subject, the sound velocity of a sound propagating through the subject holding member, and positions of image elements for the image information.

5. The subject information acquisition apparatus according to claim 1, wherein the processing section corrects positions at which the acoustic wave has arrived in accordance with Snell's law at least using the thickness of the subject holding member, the sound velocity of a sound propagating through the subject, the sound velocity of a sound propagating through the subject holding member, and positions of image elements for the image information, thereby determining weights for the electric signals to be added to one another, each of the electric signals being obtained by a corresponding one of the plurality of transformation elements.

6. The subject information acquisition apparatus according to claim 1, wherein the processing section calculates the virtual wavefronts in accordance with Snell's law at least using the thickness of the subject holding member, the sound velocity of a sound propagating through the subject holding member, the sound velocity of a sound propagating through the subject, and the arrival times of the acoustic wave from the acoustic-wave generating source, each of the virtual wavefronts being obtained by a corresponding one of the plurality of transformation elements.

7. The subject information acquisition apparatus according to claim 1, wherein the processing section assigns different levels to points constituting each of the virtual wavefronts at least using angles with respect to a corresponding one of the plurality of transformation elements as variables, the different levels corresponding to degrees of density, thereby determining weights for the virtual wavefronts to be added to one another.

8. The subject information acquisition apparatus according to claim 1, wherein the processing section calculates delay times for processing using a delay-and-sum in accordance with Snell's law at least using the thickness of the subject holding member, the sound velocity of a sound propagating through the subject holding member, the sound velocity of a sound propagating through the subject, and positions of image elements for the image information.

9. The subject information acquisition apparatus according to claim 1, wherein the processing section corrects a window function in accordance with Snell's law at least using the thickness of the subject holding member, the sound velocity of a sound propagating through the subject holding member, the sound velocity of a sound propagating through the subject, and positions of image elements for the image information, thereby determining weights for the electric signals to be subjected to processing using a delay-and-sum, each of the electric signals being obtained by a corresponding one of the plurality of transformation elements.

10. A subject information acquisition method comprising:
receiving, with each of transformation elements, an acoustic wave via a subject holding member and converting the acoustic wave into a corresponding one of electric signals, the acoustic wave being emitted from a subject; and
acquiring image information from the electric signals,
wherein arrival times of the acoustic wave from an acoustic-wave generating source are calculated in accordance with Snell's law at least using a thickness of the subject holding member, a sound velocity of a sound propagating through the subject holding member, a sound velocity of a sound propagating through the subject, and positions of image elements for the image information,
wherein the arrival times of the acoustic wave are corrected, thereby determining weights for the electric signals to be added to one another, each of the electric signals being obtained by a corresponding one of the transformation elements, and
wherein the weighted electric signals are added to one another, thereby acquiring the image information.

11. A subject information acquisition method comprising:
receiving, with each of transformation elements, an acoustic wave via a subject holding member and converting the acoustic wave into a corresponding one of electric signals, the acoustic wave being emitted from a subject; and
acquiring image information from the electric signals,
wherein virtual wavefronts of the acoustic wave are calculated in accordance with Snell's law at least using a thickness of the subject holding member, a sound velocity of a sound propagating through the subject holding member, a sound velocity of a sound propagating through the subject, and arrival times of the acoustic wave from an acoustic-wave generating source, each of the virtual wavefronts being calculated for a corresponding one of the transformation elements,
wherein different levels are assigned to points constituting each of the virtual wavefronts using angles with respect to a corresponding one of the transformation elements as variables, thereby determining weights for the virtual wavefronts to be added to one another, the different levels corresponding to degrees of density, and
wherein the weighted virtual wavefronts are added to one another, thereby acquiring the image information.

12. A subject information acquisition method comprising:
receiving, with each of transformation elements, an acoustic wave via a subject holding member and converting the acoustic wave into a corresponding one of electric signals, the acoustic wave being emitted from a subject; and
acquiring image information from the electric signals,
wherein delay times for processing using a delay-and-sum are calculated in accordance with Snell's law at least using a thickness of the subject holding member, a sound velocity of a sound propagating through the subject holding member, a sound velocity of a sound propagating through the subject, and positions of image elements for the image information,
wherein a window function is corrected, thereby determining weights for the electric signals to be subjected to processing using the delay-and-sum, each of the electric signals being obtained by a corresponding one of the transformation elements, and
wherein the weighted electric signals are subjected to processing using the delay-and-sum, thereby acquiring the image information.

* * * * *